US012622683B2

(12) United States Patent
Onoda

(10) Patent No.: US 12,622,683 B2
(45) Date of Patent: May 12, 2026

(54) BIOPSY DEVICE AND PROGRAM

(71) Applicant: FUJIFILM CORPORATION, Tokyo (JP)

(72) Inventor: Atsushi Onoda, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/817,244

(22) Filed: Aug. 28, 2024

(65) Prior Publication Data

US 2025/0090147 A1 Mar. 20, 2025

(30) Foreign Application Priority Data

Sep. 15, 2023 (JP) ................................. 2023-150481

(51) Int. Cl.
| | |
|---|---|
| *A61B 10/02* | (2006.01) |
| *A61B 10/00* | (2006.01) |
| *A61B 34/10* | (2016.01) |
| *A61B 34/20* | (2016.01) |

(52) U.S. Cl.
CPC ...... *A61B 10/0266* (2013.01); *A61B 10/0041* (2013.01); *A61B 34/10* (2016.02); *A61B 34/20* (2016.02); *A61B 2010/0208* (2013.01); *A61B 10/0233* (2013.01); *A61B 2034/107* (2016.02); *A61B 2034/2074* (2016.02)

(58) Field of Classification Search
CPC ............ A61B 10/0266; A61B 10/0041; A61B 10/0233; A61B 34/10; A61B 34/20; A61B 2010/0208; A61B 2034/107; A61B 2034/2074; G16H 30/02
See application file for complete search history.

(56) References Cited

U.S. PATENT DOCUMENTS

| | | | | |
|---|---|---|---|---|
| 6,671,538 B1 * | 12/2003 | Ehnholm | ............... | A61B 34/20 |
| | | | | 600/425 |
| 2003/0114862 A1 * | 6/2003 | Chu | ...................... | A61B 90/11 |
| | | | | 606/130 |
| 2007/0293787 A1 * | 12/2007 | Taylor | ................ | A61B 10/0266 |
| | | | | 600/562 |
| 2011/0087132 A1 * | 4/2011 | DeFreitas | .............. | A61B 90/11 |
| | | | | 378/62 |
| 2011/0116602 A1 * | 5/2011 | Sakaguchi | ............. | A61B 6/502 |
| | | | | 378/98.5 |
| 2013/0108138 A1 * | 5/2013 | Nakayama | ............. | A61B 6/466 |
| | | | | 382/132 |
| 2016/0183887 A1 | 6/2016 | Toba | | |

(Continued)

FOREIGN PATENT DOCUMENTS

| | | |
|---|---|---|
| JP | 2012-157689 A | 8/2012 |
| JP | 2016-120025 A | 7/2016 |

(Continued)

*Primary Examiner* — Sean D Mattson
(74) *Attorney, Agent, or Firm* — SOLARIS Intellectual Property Group, PLLC

(57) ABSTRACT

A controller includes a display controller that performs control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states.

13 Claims, 15 Drawing Sheets

(56) References Cited

U.S. PATENT DOCUMENTS

| 2016/0310215 | A1 * | 10/2016 | Palma | .................... | A61B 34/10 |
| 2017/0071672 | A1 * | 3/2017 | Shochat | .................... | G06T 7/11 |
| 2018/0132944 | A1 * | 5/2018 | Yan | .......................... | A61B 8/12 |
| 2018/0338795 | A1 * | 11/2018 | Sugiyama | .............. | A61B 34/10 |
| 2021/0196389 | A1 * | 7/2021 | Yi | .......................... | G16H 30/40 |
| 2021/0330387 | A1 * | 10/2021 | Nakamura | ............. | A61B 34/20 |
| 2021/0343088 | A1 * | 11/2021 | Payyavula | ........... | A61B 1/0676 |

FOREIGN PATENT DOCUMENTS

| JP | 2018-198816 A | 12/2018 | | |
| WO | WO-2011083412 A1 * | 7/2011 | ............. | A61B 34/10 |

* cited by examiner

FIG. 2
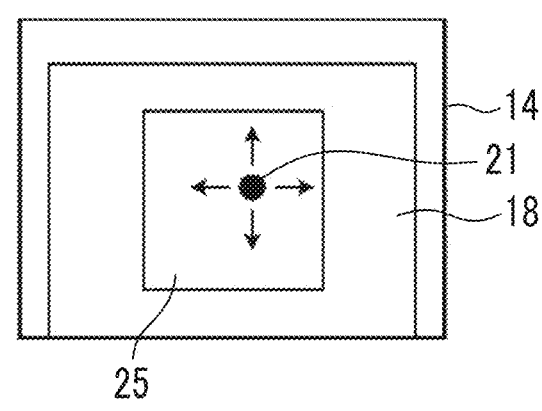
FIG. 3
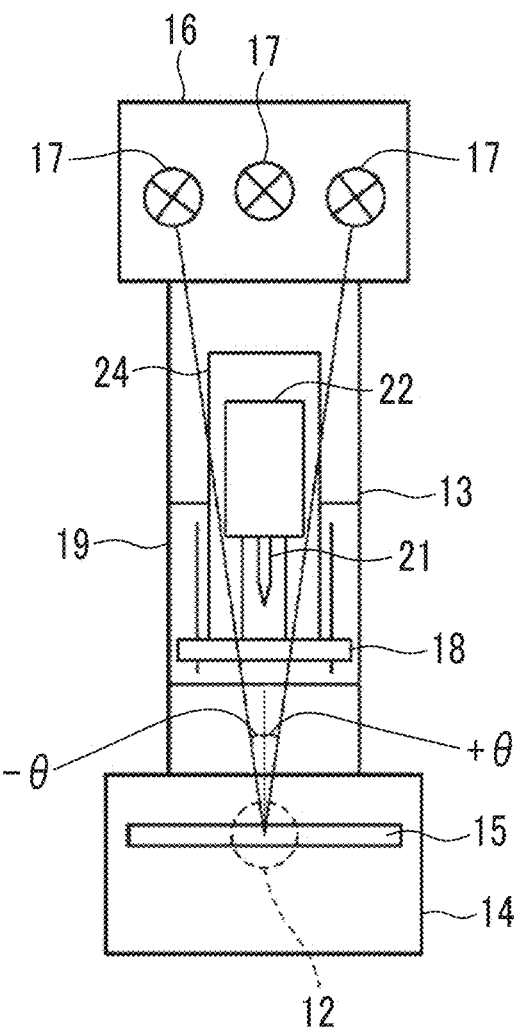
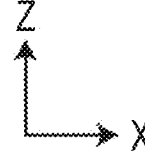

FIG. 8

BIOPSY NEEDLE INFORMATION DATABASE

| USE | BIOPSY NEEDLE ID | THICKNESS | LENGTH | OPENING PORTION | | | | IMAGE INFORMATION |
|---|---|---|---|---|---|---|---|---|
| | | | | POSITION | SIZE | | | |
| LONGITUDINAL PUNCTURE | NV01 | (THICKNESS 1) | (LENGTH 1) | (POSITION 1) | (SIZE 1) | · · · | · · · | (IMAGE INFORMATION 1) |
| | NV02 | (THICKNESS 2) | (LENGTH 2) | (POSITION 2) | (SIZE 2) | · · · | · · · | (IMAGE INFORMATION 2) |
| | · · · | · · · | · · · | · · · | · · · | · · · | · · · | · · · |
| LATERAL PUNCTURE | NH001 | (THICKNESS X) | (LENGTH X) | (POSITION X) | (SIZE X) | · · · | · · · | (IMAGE INFORMATION X) |
| | · · · | · · · | · · · | · · · | · · · | · · · | · · · | · · · |

BIOPSY DEVICE AND PROGRAM

CROSS-REFERENCE TO RELATED APPLICATION

This application claims priority from Japanese Patent Application No. 2023-150481, filed Sep. 15, 2023, the disclosure of which is incorporated herein by reference in its entirety.

BACKGROUND

Technical Field

The present disclosure relates to a biopsy device and a non-transitory computer-readable storage medium storing a program.

Related Art

JP2018-198816A discloses a breast X-ray imaging apparatus that is intended to enable a more reliable collection of a specimen including a lesion part.

The breast X-ray imaging apparatus comprises a collection unit that collects three-dimensional image data of a breast of a subject, a detection unit that detects a lesion part from the three-dimensional image data, and a derivation unit that analyzes linearity of a three-dimensional distribution of the lesion part and derives a puncture path in which a puncture needle is inserted into the breast based on an analysis result of the linearity.

Further, in the breast X-ray imaging apparatus, a graphic indicating a puncture path and a puncture depth of a puncture needle is displayed on an operation screen.

Note that the puncture needle in this technology is also referred to as a biopsy needle, a biological needle, or the like. In this specification, the puncture needle is consistently described as a "biopsy needle".

However, in the technology disclosed in JP2018-198816A, although a graphic indicating a puncture path and a puncture depth of a biopsy needle is displayed, it is difficult to recognize an actual position relationship of the biopsy needle with respect to the graphic. As a result, in the technology, there is a problem that it is not easy to compare a target state of the biopsy needle with an actual state of the biopsy needle.

SUMMARY

The present disclosure has been made in view of the above circumstances, and an object of the present disclosure is to provide a biopsy device and a non-transitory computer-readable storage medium storing a program capable of easily comparing a target state of a biopsy needle with an actual state of the biopsy needle, as compared with the technology in the related art.

In order to achieve the above object, according to a first aspect of the present disclosure, there is provided a biopsy device comprising: at least one processor, in which the processor is configured to: perform control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states.

According to a second aspect of the present disclosure, in the biopsy device according to the first aspect, the processor is configured to: in a case where the first image and the second image overlap with each other by a movement operation of the biopsy needle, perform control such that at least one of the first image or the second image is displayed in a state different from a previous display state.

According to a third aspect of the present disclosure, in the biopsy device according to the second aspect, the processor is configured to: further perform control to display, separately from the display diagram, an operation reception region for receiving an input of an operation instruction for the biopsy needle; and in a case where the first image and the second image overlap with each other by a movement operation of the biopsy needle, set a display state of the operation reception region to a state different from a previous display state.

According to a fourth aspect of the present disclosure, in the biopsy device according to the second aspect or the third aspect, the processor is configured to: in a case where the first image and the second image overlap with each other by a movement operation of the biopsy needle, perform control such that the biopsy needle is not moved to an insertion side of the target object.

According to a fifth aspect of the present disclosure, in the biopsy device according to the first aspect, the processor is configured to: further perform control to display auxiliary lines disposed at equal intervals in a region including the first image and the target image in the display diagram.

According to a sixth aspect of the present disclosure, in the biopsy device according to the fifth aspect, the processor is configured to: perform control to incline and display the auxiliary lines in accordance with a traveling direction of the biopsy needle toward the target object.

According to a seventh aspect of the present disclosure, in the biopsy device according to the first aspect, the processor is configured to: further perform control to display a third image indicating a direction of a body of a subject including the target object, separately from the display of the display diagram.

According to an eighth aspect of the present disclosure, in the biopsy device according to the first aspect, the processor is configured to: in a case where an instruction to adjust the position of the first image is received, further perform control to display a first mark indicating the position in an initial state and a second mark indicating the adjusted position in different states.

According to a ninth aspect of the present disclosure, in the biopsy device according to the first aspect, the processor is configured to: further perform control to display, in the display diagram, a boundary line with a region where a problem may occur in a case where the biopsy needle is moved.

According to a tenth aspect of the present disclosure, in the biopsy device according to the ninth aspect, the processor is configured to: in a case where the region where a problem may occur is not a region into which the biopsy needle is allowed to be inserted, prohibit control to display the boundary line.

According to an eleventh aspect of the present disclosure, in the biopsy device according to the first aspect, the processor is configured to: in a case where the biopsy needle punctures a breast as the target object in a state where the breast is compressed by a compression plate against an imaging table of a mammography apparatus, further perform control to display an additional image indicating at least one of the imaging table or the compression plate.

According to a twelfth aspect of the present disclosure, in the biopsy device according to the first aspect, the first image is an image indicating the target position and a target direction of the biopsy needle, and the second image is an image indicating the actual position and an actual direction of the biopsy needle.

According to a thirteenth aspect of the present disclosure, in the biopsy device according to the first aspect, at least one of the first image or the second image is an image in which the biopsy needle is symbolized.

Further, in order to achieve the above object, according to a fourteenth aspect of the present disclosure, there is provided a non-transitory computer-readable storage medium storing a program that causes a computer to execute a process, the process comprising: performing control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states.

According to the present disclosure, it is possible to easily compare a target state of a biopsy needle with an actual state of the biopsy needle, as compared with the technology in the related art.

BRIEF DESCRIPTION OF THE DRAWINGS

FIG. 2 is a schematic plan view of a compression plate in the mammography apparatus according to the embodiment, viewed from above.

FIG. 3 is a diagram illustrating an example of a state in a case where a radiation irradiator in the mammography apparatus according to the embodiment is inclined in a right-left direction from a direction along an arm.

FIG. 8 is a schematic diagram illustrating an example of a configuration of a biopsy needle information database according to the embodiment.

DETAILED DESCRIPTION

Figure 1:
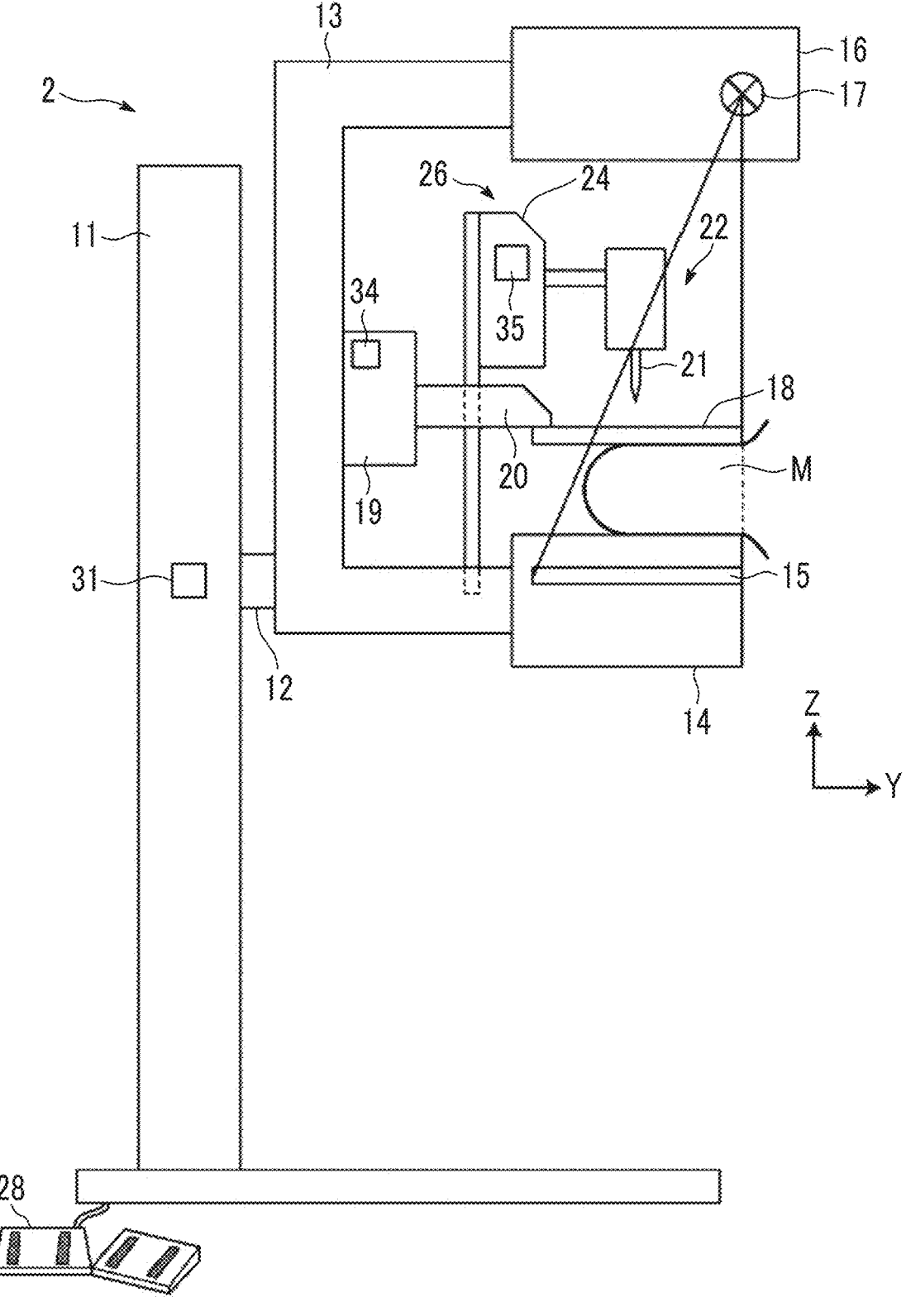
FIG. 1 is a schematic configuration diagram illustrating an example of a mammography apparatus according to an embodiment.

Hereinafter, an example of an embodiment for implementing the technology of the present disclosure will be described in detail with reference to the drawings. First, a mammography apparatus 2 according to the present embodiment will be described in detail with reference to FIG. 1 to FIG. 4. FIG. 1 is a schematic configuration diagram illustrating an example of the mammography apparatus 2 according to the present embodiment.

As an example, as illustrated in FIG. 1, in the mammography apparatus 2 according to the present embodiment, a radiation housing unit 16 in which a radiation irradiator 17 is housed inside and an imaging table 14 are connected to an arm 13 to face each other. An image recording medium such as a radiation detector 15 is set inside the imaging table 14 in a state of being housed in a recording medium holding portion such as a cassette. The arm 13 is attached to a base 11 with a C axis 12. In addition, the arm 13 is provided to the base 11 by attaching the C axis 12, which is the center of rotation, to a center position of the radiation detector 15 such that the center of rotation of the arm 13 is the center of the radiation detector 15 in an X direction (refer to FIG. 2).

The base 11 is provided with an operation unit 28 that receives an instruction for radiation irradiation from the radiation irradiator 17 and allows an operator to adjust a height of the imaging table 14 (that is, a height of the arm 13) and an inclination of the imaging table 14 (that is, an inclination of the arm 13), and with an arm controller 31 that moves the arm 13 vertically and rotationally according to an input from the operation unit 28.

The arm controller 31 adjusts the inclination of the arm 13 by rotating the C axis 12 attached to the base 11, and adjusts the height of the imaging table 14 by vertically moving the arm 13.

At a central portion of the arm 13, a compression plate 18 that is disposed above the imaging table 14 to hold and compress the breast, a support portion 20 that supports the compression plate 18, and a moving mechanism 19 that moves the support portion 20 in an up-down direction along the arm 13. The position and compression pressure of the compression plate 18 are controlled by a compression plate controller 34.

FIG. 2 is a view of the compression plate 18 viewed from above. As illustrated in FIG. 2, the compression plate 18 is provided with an opening portion 25 of approximately 10×10 cm square such that a biopsy can be performed on the breast fixed by the imaging table 14 and the compression plate 18.

As an example, a biopsy unit 26 as a biopsy device of the present disclosure illustrated in FIG. 1 comprises a biopsy needle 21 that is inserted into a breast and a biopsy needle unit 22, and further comprises a moving mechanism 24 that moves the biopsy needle unit 22 in X, Y, and Z directions. The position of a distal end of the biopsy needle 21 of the biopsy needle unit 22 is controlled by a needle position controller 35 of the moving mechanism 24. Note that, in FIG. 2, a horizontal direction is the X direction, a vertical direction is the Y direction, and a direction perpendicular to an XY plane is the Z direction.

Note that the mammography apparatus 2 acquires scout images which include a target region of the breast to be biopsied and are imaged from two directions before puncture is performed. The scout image is an image viewed from different viewpoints in order to confirm the position to be pathologically examined. For example, as illustrated in FIG. 3, two partial images obtained by performing imaging from directions in which the radiation irradiator 17 is inclined in a right-left direction (for example, inclined by 15° in the directions of $+\theta$ and $-\theta$ illustrated in FIG. 3) from a direction along the arm 13 are set as the scout images.

Figure 4:
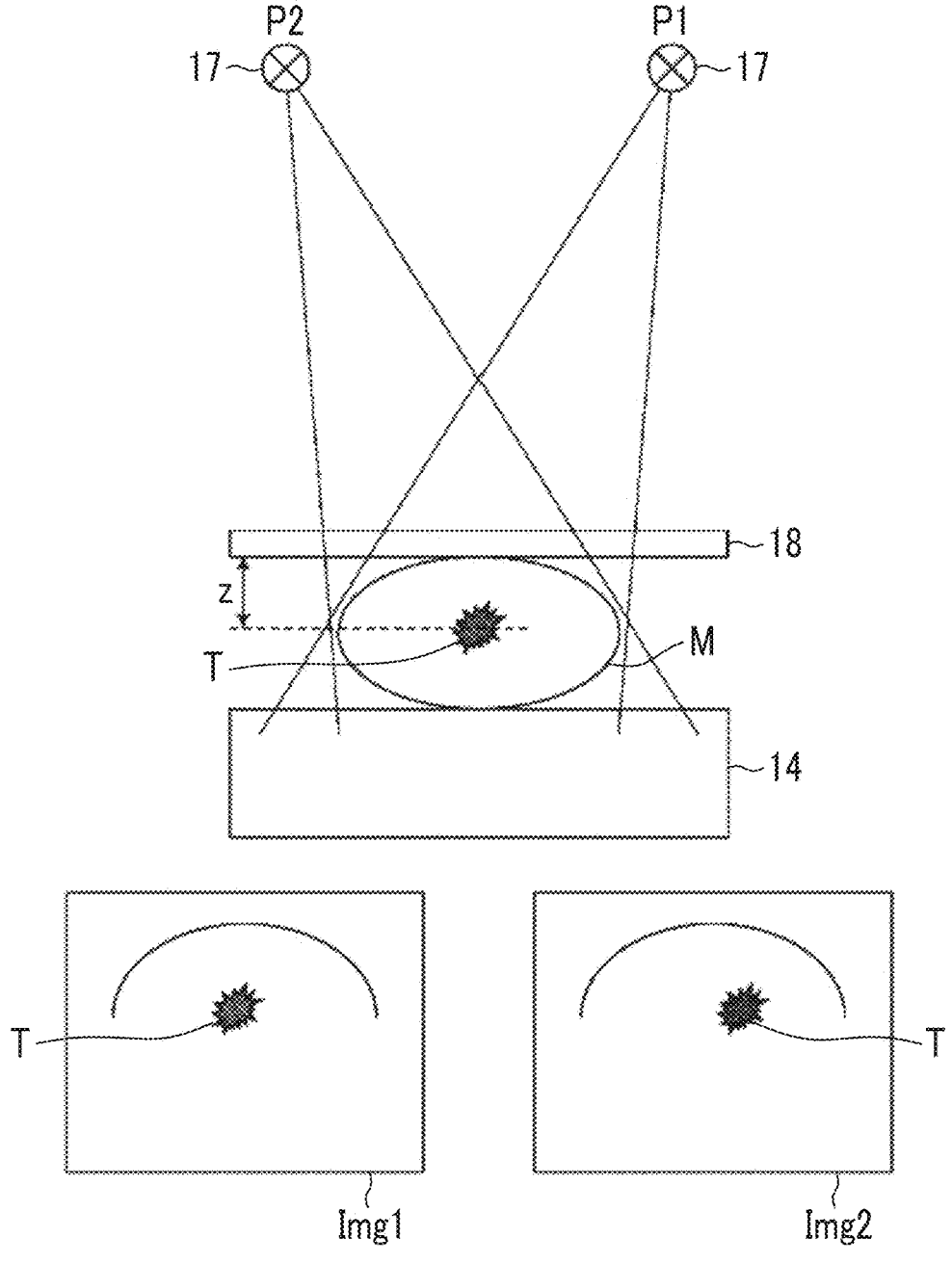
FIG. 4 is a diagram illustrating an example of a relationship between positions of a radiation irradiator in the mammography apparatus according to the embodiment and two scout images.

FIG. 4 is a diagram illustrating an example of a relationship between the positions of the radiation irradiator 17 and two scout images. In a scout image Img1 obtained by performing imaging in a state where the radiation irradiator 17 is placed at a position P1, a position of a target T appears to be close to the left side, and in a scout image Img2 obtained by performing imaging in a state where the radiation irradiator 17 is placed at a position P2, a position of a target T appears to be close to the right side. From the deviation of the target T between the two scout images Img1 and Img2, a distance z from a bottom surface of the compression plate 18 (the side that presses the breast) to the target T and the position of the target T on the XY plane are obtained, and thus, a three-dimensional position of the target T can be obtained.

The needle position controller 35 of the biopsy unit 26 moves a position of a distal end of the biopsy needle 21 to a position of the target T and performs biopsy on the breast using the biopsy needle 21, under a control of a controller 70 (also refer to FIG. 5) that is provided in the biopsy unit 26 and is to be described in detail below.

Figure 5:
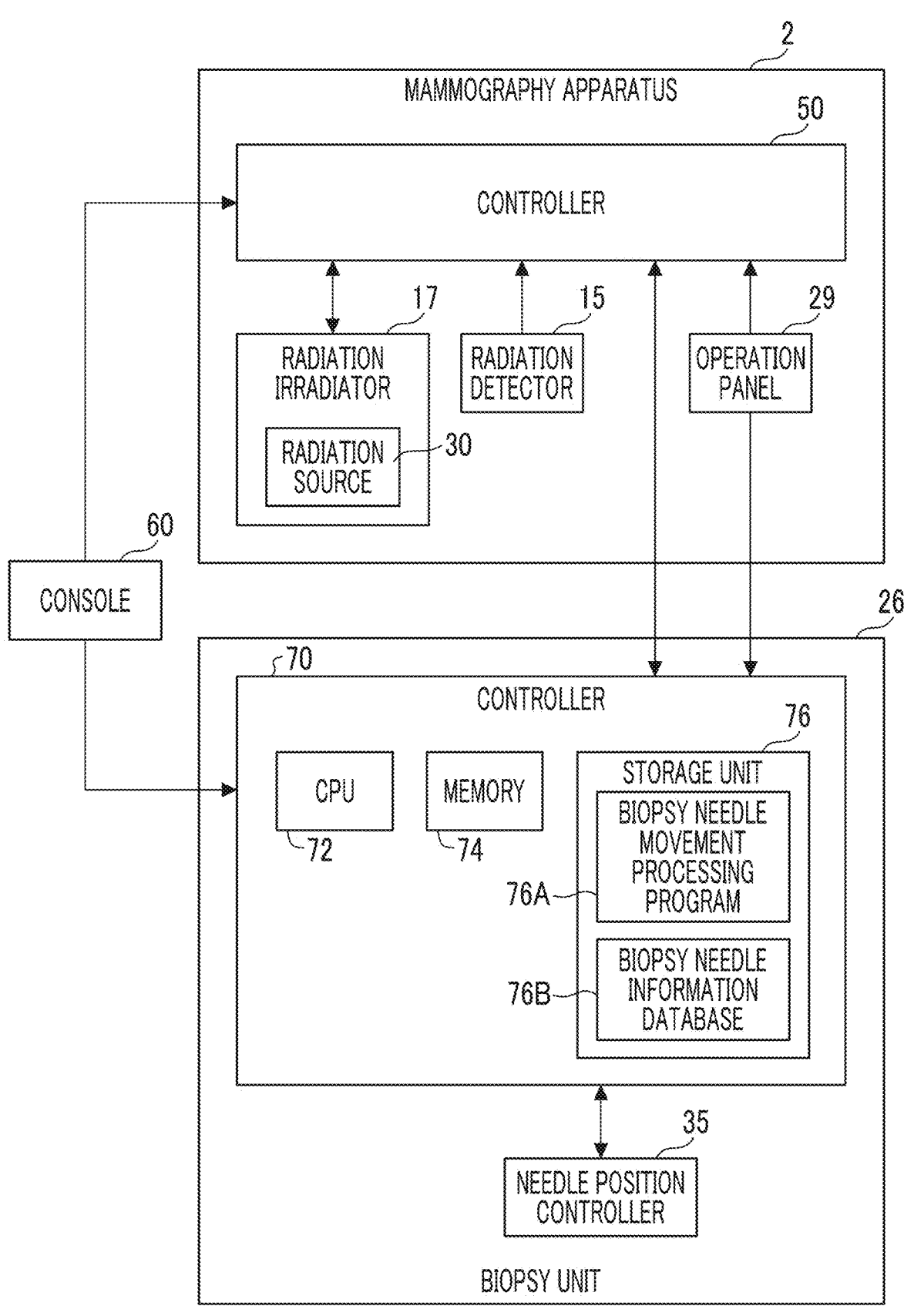
FIG. 5 is a block diagram illustrating an example of an electrical configuration of the mammography apparatus and a biopsy unit according to the embodiment.

Next, an electrical configuration of the mammography apparatus 2 and the biopsy unit 26 according to the present embodiment will be described with reference to FIG. 5. FIG. 5 is a block diagram illustrating an example of the electrical configuration of the mammography apparatus 2 and the biopsy unit 26 according to the present embodiment.

The mammography apparatus 2 according to the present embodiment includes an operation panel 29 and a controller 50 in addition to the radiation detector 15, the radiation irradiator 17, and the like.

The controller 50 has functions to control the entire operation of the mammography apparatus 2, and comprises a central processing unit (CPU) as a processor, a memory including a read only memory (ROM) and a random access memory (RAM), and a nonvolatile storage unit including a hard disk drive (HDD), a flash memory, and the like. In addition, the controller 50 is connected to the radiation irradiator 17, the radiation detector 15, the biopsy unit 26, and the operation panel 29.

In a case where the controller 50 receives an irradiation instruction from the operator via the operation panel 29 (exposure switch), the controller 50 causes a radiation source 30 provided in the radiation irradiator 17 to irradiate an upper surface of the imaging table 14 with radiation according to an imaging menu set on the basis of designated exposure conditions.

The radiation detector 15 receives irradiation of radiation carrying image information and records the image information, and outputs the recorded image information. For example, the radiation detector 15 is configured as a flat panel detector (FPD) that includes a radiation-sensitive layer and converts radiation into digital data and outputs the digital data. In a case where the radiation detector 15 is irradiated with radiation, the radiation detector 15 outputs the image information indicating the radiation image to the controller 50. In the present embodiment, the radiation detector 15 receives irradiation of the radiation that has passed through a breast M, and thus, the image information indicating the radiation image is obtained.

The operation panel 29 has a function of setting various types of operation information such as exposure conditions and posture information, various operation instructions, and the like.

The exposure conditions that are set in the operation panel 29 include information such as a tube voltage, a tube current, an irradiation time, and posture information. The posture information designated in the operation panel 29 includes information representing an imaging position (imaging posture, angle) in a case of imaging the breast M from a plurality of directions.

Note that various types of operation information such as the exposure conditions and the posture information, various operation instructions, and the like may be set by the operator using the operation panel 29, may be obtained from another control device (a radiology information system (RIS), a radiation information system, or a system that manages information on medical treatment, diagnosis, and the like using radiation) or the like, or may be stored in advance in a storage unit.

In a case where various types of information are set via the operation panel 29, the controller 50 causes the radiation irradiator 17 to irradiate an imaging part (breast M) of a subject with radiation according to the imaging menu which is set based on the various types of set information, and performs imaging of a radiation image. In a case of performing tomosynthesis imaging in which imaging is performed from a plurality of directions, the controller 50 adjusts a posture of the arm 13 such that the radiation irradiator 17 is positioned above the upper surface of the imaging table 14. In addition, in a state substantially similar to the state illustrated in FIG. 3, the controller 50 causes the radiation source 30 provided in the radiation irradiator 17 to individually irradiate the upper surface of the imaging table 14 with radiation at different angles based on the imaging condition by rotating the arm 13 to move the radiation irradiator 17 in an arc shape from a predetermined initial angle by a predetermined interval angle. Thereby, a plurality of radiation images can be obtained.

On the other hand, the biopsy unit 26 according to the present embodiment includes a controller 70 in addition to the needle position controller 35 and the like.

The controller 70 has a function of controlling the entire operation of the biopsy unit 26, and includes a CPU 72 as a processor, a memory 74 including a ROM and a RAM, and a non-volatile storage unit 76 configured with an HDD, a flash memory, and the like. In addition, the controller 70 is connected to the needle position controller 35 and the operation panel 29.

The controller 70 controls movement of the biopsy needle 21 provided in the biopsy needle unit 22 by executing biopsy needle movement processing to be described in detail below. The needle position controller 35 provided in the biopsy unit 26 moves the biopsy needle 21 to a predetermined position by driving the moving mechanism 24 in response to an instruction from the controller 70, and holds the biopsy needle 21 in a state where the biopsy needle 21 is inclined at an insertion angle.

The operation panel 29 according to the present embodiment is provided with a display unit that is configured with a liquid crystal display or the like and is for displaying various types of information, and also has a function of displaying a biopsy needle movement support screen (also refer to FIG. 10) to be described in detail below in a case of performing puncture of the breast M by the biopsy unit 26. In addition, the display unit of the operation panel 29 according to the present embodiment is a so-called touch panel display provided with a touch panel, and various buttons that are displayed as soft switches on the biopsy needle movement support screen displayed on the display unit can be directly designated.

Further, the storage unit 76 that is a storage medium provided in the controller 70 according to the present embodiment stores a biopsy needle movement processing program 76A. The CPU 72 reads out the biopsy needle movement processing program 76A from the storage unit 76, expands the read-out biopsy needle movement processing program 76A in the memory 74, and executes the expanded biopsy needle movement processing program 76A. Further, the storage unit 76 stores a biopsy needle information database 76B. The biopsy needle information database 76B will be described in detail below.

In addition, as illustrated in FIG. 5, a console 60 dedicated to the mammography apparatus 2 is connected to the mammography apparatus 2 and the biopsy unit 26 according to the present embodiment, and the mammography apparatus 2 and the biopsy unit 26 can acquire various types of information from the console 60.

The information acquired from the console 60 by the biopsy unit 26 according to the present embodiment includes biopsy needle specifying information (in the present embodiment, a biopsy needle identification (ID) to be described later) that is information for specifying the biopsy needle 21 used in the biopsy unit 26.

The controller 70 acquires the biopsy needle specifying information from the console 60, sets the biopsy needle 21 specified by the acquired biopsy needle specifying information as a target, and controls movement of the biopsy needle 21 in cooperation with the needle position controller 35.

Figure 6:
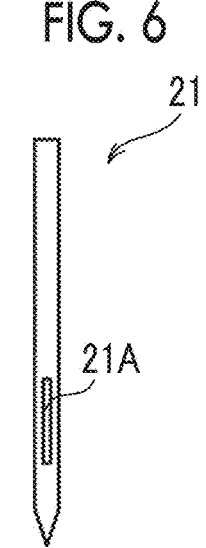
FIG. 6 is a front view illustrating an example of a configuration of a biopsy needle according to the embodiment.

Next, the biopsy needle 21 according to the present embodiment will be described with reference to FIG. 6. FIG. 6 is a front view illustrating an example of a configuration of the biopsy needle 21 according to the present embodiment.

As illustrated in FIG. 6 as an example, the biopsy needle 21 according to the present embodiment has a sharp tip part, and has a hollow shape. An opening portion 21A that communicates with an inner space is provided in the vicinity of the tip part.

The opening portion 21A is for introducing a tissue which is a puncture target into the biopsy needle 21, and the opening portion 21A according to the present embodiment has a rectangular shape in a front view. On the other hand, the present disclosure is not limited thereto. For example, a form in which an opening having a circular shape or an elliptical shape in a front view is applied as the opening portion 21A may be adopted.

The biopsy unit 26 according to the present embodiment can perform not only longitudinal puncture in which the puncture direction of the biopsy needle 21 is a direction perpendicular to the imaging surface of the imaging table 14 but also lateral puncture in which the puncture direction of the biopsy needle 21 is a direction parallel to the imaging surface of the imaging table 14. On the other hand, the present disclosure is not limited thereto. For example, a form in which the biopsy unit 26 can perform only longitudinal puncture may be adopted.

Further, the biopsy unit 26 according to the present embodiment selectively applies, as the applicable biopsy needle 21, a biopsy needle suitable for the purpose of puncture from a plurality of types of biopsy needles each of which differs in manufacturer, size, position of the opening portion 21A, and the like. On the other hand, the present disclosure is not limited thereto. For example, a form in which only one type of dedicated biopsy needle is applied to the biopsy unit 26 as the biopsy needle 21 may be adopted.

Figure 7:
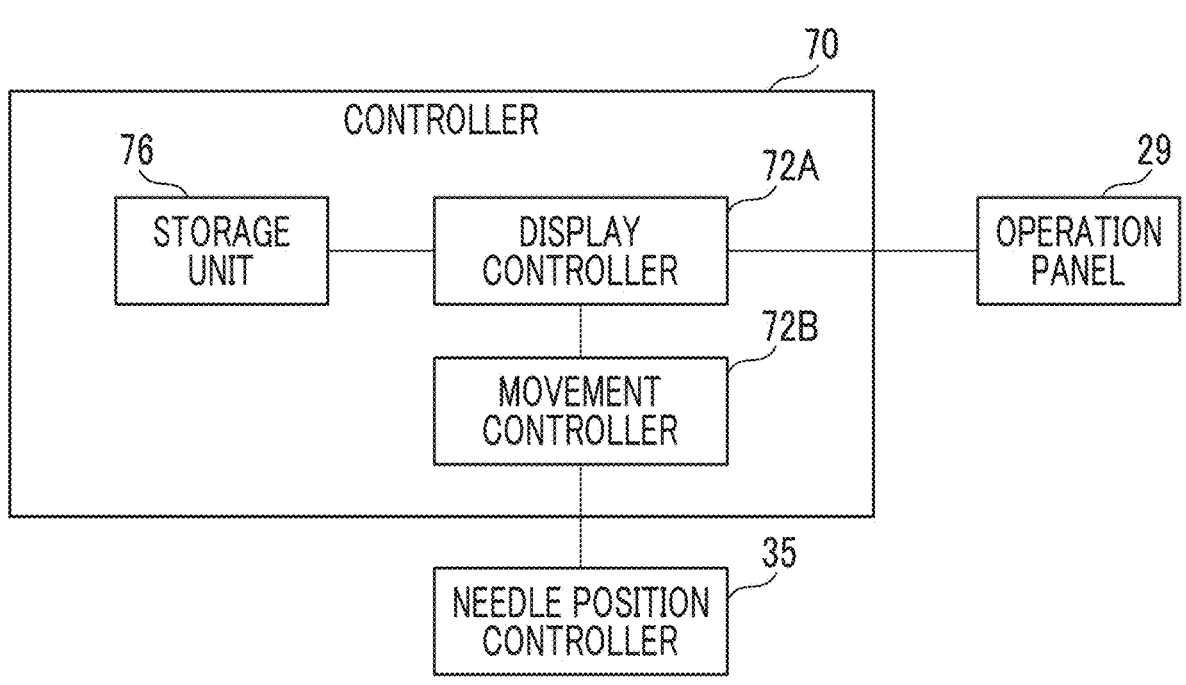
FIG. 7 is a functional block diagram illustrating a functional configuration of a controller provided in the biopsy unit according to the embodiment.

Next, a functional configuration of the controller 70 according to the present embodiment will be described with reference to FIG. 7. FIG. 7 is a functional block diagram illustrating a functional configuration of the controller 70 provided in the biopsy unit 26 according to the present embodiment.

As illustrated in FIG. 7, the controller 70 according to the present embodiment includes a display controller 72A and a movement controller 72B. In a case where the CPU 72 executes the biopsy needle movement processing program 76A, the controller 70 functions as the display controller 72A and the movement controller 72B.

The display controller 72A according to the present embodiment performs control to display a target image indicating a target object (in the present embodiment, the breast M) from which a tissue is to be collected by the biopsy needle 21, a first image indicating a target position of the biopsy needle 21, and a second image indicating an actual position of the biopsy needle 21 in the same display diagram with a common two-dimensional coordinate system, and to display the first image and the second image in different states. In the present embodiment, a form in which the display of the display diagram is performed by the display unit provided in the operation panel 29 has been described. On the other hand, the present disclosure is not limited thereto. For example, the display of the display diagram may be performed by a display unit of another device, such as a display unit provided in the console 60.

Note that, in the present embodiment, although images in which the biopsy needle 21 is symbolized are applied as the first image and the second image, the present disclosure is not limited thereto. For example, a form in which the images of the biopsy needle 21 itself are applied as the first image and the second image may be adopted, or a form in which one of the first image and the second image is an image in which the biopsy needle 21 is symbolized and the other of the first image and the second image is an image of the biopsy needle 21 itself may be adopted.

Further, in the present embodiment, as described above, since the biopsy needle 21 is held in a state of being inclined at the insertion angle, only the position of the biopsy needle 21 is set as a control target of movement. On the other hand, the present disclosure is not limited thereto. In a case where the insertion angle of the biopsy needle 21 is also variable, a form in which both a position and a direction (posture) of the biopsy needle 21 are set as control targets of movement may be adopted. In this case, the display controller 72A performs control to display the target image indicating the target object, the first image indicating the target position and the target direction of the biopsy needle 21, and the second image indicating the actual position and the actual direction of the biopsy needle 21 in the display diagram, and to display the first image and the second image in different states.

Further, in a case where the first image and the second image overlap with each other by the movement operation of the biopsy needle 21, the display controller 72A according to the present embodiment performs control to display at least one of the first image or the second image (in the present embodiment, only the second image) in a state different from the previous display state. In addition, the display controller 72A according to the present embodiment further performs control to display an operation reception region for receiving an input of an operation instruction for the biopsy needle 21, separately from the display diagram. In addition, in a case where the first image and the second image overlap with each other by the movement operation of the biopsy needle 21, the display controller 72A according to the present embodiment sets a display state of the operation reception region to a state different from the previous display state.

On the other hand, the movement controller 72B according to the present embodiment performs control such that the biopsy needle 21 is not moved to the insertion side of the target object in a case where the first image and the second image overlap with each other by the movement operation of the biopsy needle 21. With this control, it is possible to prevent the biopsy needle 21 from being inserted to an unnecessary depth.

In addition, the display controller 72A according to the present embodiment further performs control to display auxiliary lines disposed at equal intervals in a region including the first image and the target image in the display diagram. In particular, the display controller 72A according to the present embodiment performs control such that the auxiliary lines are inclined and displayed in accordance with a traveling direction of the biopsy needle 21 toward target object. By displaying the auxiliary lines, it is possible to more accurately recognize a deviation amount between the actual state and the target state of the biopsy needle 21.

Further, the display controller 72A according to the present embodiment further performs control to display a third image indicating a direction of the body of the subject including the target object, separately from the display diagram. Further, in a case where an instruction to adjust the position of the first image is received, the display controller 72A according to the present embodiment further performs control to display a first mark indicating the position in an initial state and a second mark indicating the adjusted position in different states.

Further, the display controller 72A according to the present embodiment further performs control to display, on the display diagram, a boundary line with a region where a problem may occur in a case where the biopsy needle 21 is moved. In particular, the display controller 72A according to the present embodiment prohibits the control to display the boundary line in a case where the region where a problem may occur is not a region into which the biopsy needle 21 is to be inserted.

In addition, the display controller 72A according to the present embodiment further performs control to display an additional image indicating at least one (in the present embodiment, both) of the imaging table 14 or the compression plate 18 in a case where the biopsy needle 21 punctures the breast M as the target object in a state of being compressed by the compression plate 18 against the imaging table 14 of the mammography apparatus 2.

Next, the biopsy needle information database 76B according to the present embodiment will be described with reference to FIG. 8. FIG. 8 is a schematic diagram illustrating an example of a configuration of the biopsy needle information database 76B according to the present embodiment.

The biopsy needle information database 76B according to the present embodiment is a database in which information related to the biopsy needle 21 corresponding to the biopsy unit 26 according to the present embodiment is registered. As illustrated in FIG. 8, in the biopsy needle information database 76B according to the present embodiment, pieces of information, such as a use, a biopsy needle ID, a thickness, a length, an opening portion, and image information, are stored by being associated with each other.

The use is information indicating whether the biopsy needle is for longitudinal puncture or lateral puncture, and the biopsy needle ID is information indicating the biopsy needle ID itself.

In addition, the thickness and the length are pieces of information indicating a thickness and a length of the corresponding biopsy needle 21, and the opening portion is information indicating a state of the opening portion 21A provided in the corresponding biopsy needle 21, such as a position and a size of the opening portion 21A.

Further, the image information is information indicating the first image and second image of the corresponding biopsy needle 21. In the present embodiment, a common image obtained by imitating a shape of the corresponding biopsy needle 21 is applied as the first image and the second image. On the other hand, the present disclosure is not limited thereto. For example, one of the first image and the second image may be an image obtained by imitating the shape of the corresponding biopsy needle 21, and the other of the first image and the second image may be an image obtained by simplifying the shape of the corresponding biopsy needle 21 (for example, a simple straight line image) or the like.

Figure 9:
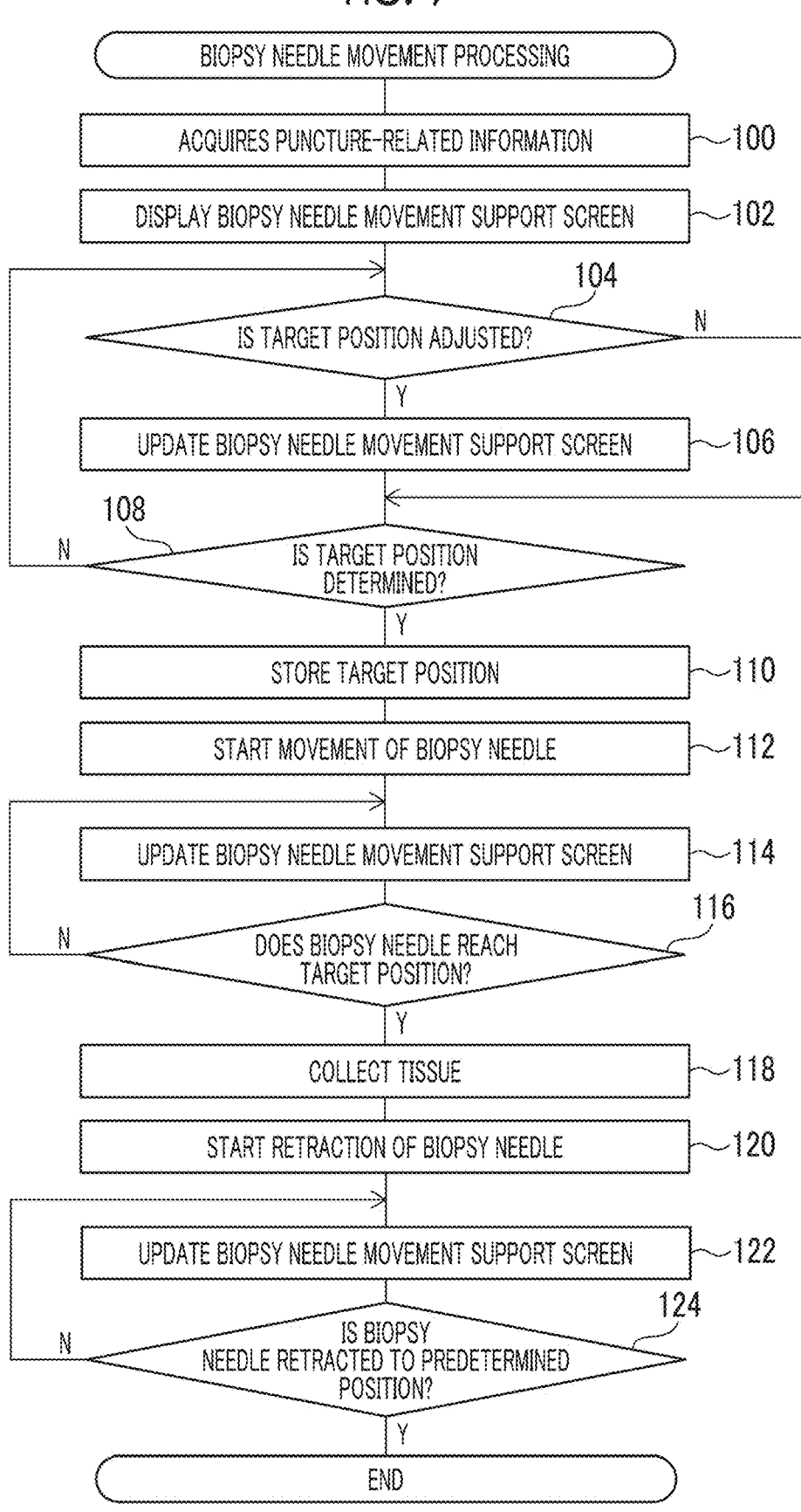
FIG. 9 is a flowchart illustrating an example of biopsy needle movement processing according to the embodiment.

Next, an operation of the biopsy unit 26 according to the present embodiment will be described with reference to FIG. 9 to FIG. 14. FIG. 9 is a flowchart illustrating an example of biopsy needle movement processing according to the present embodiment. Further, FIG. 10 is a front view illustrating an example of a biopsy needle movement support screen according to the present embodiment, and FIG. 11 to FIG. 14 are front views illustrating other examples of the biopsy needle movement support screen according to the present embodiment.

In a case where the CPU 72 in the controller 70 of the biopsy unit 26 executes the biopsy needle movement processing program 76A, the biopsy needle movement processing illustrated in FIG. 9 is executed. The biopsy needle movement processing illustrated in FIG. 9 is executed, for example, in a case where the biopsy unit 26 provided with the biopsy needle 21 is attached to the mammography apparatus 2 and the mammography apparatus 2 is ready to perform imaging on the breast M that is a target, and in a case where various types of information (hereinafter, referred to as "puncture-related information") for performing puncture using the biopsy unit 26 are input via the console 60. Here, the puncture-related information includes the above-described biopsy needle specifying information that is for specifying the mounted biopsy needle 21 (in the present embodiment, the biopsy needle ID), and information (hereinafter, referred to as "target position information") indicating a three-dimensional position (hereinafter, referred to as a "target position") of a target T (a target tissue of the puncture) obtained from the above-described scout image. Note that, in order to avoid confusion, here, a case where the biopsy needle information database 76B is already constructed will be described.

In step 100 of FIG. 9, the CPU 72 acquires the puncture-related information that is input via the console 60. In step 102, the CPU 72 reads out information corresponding to the biopsy needle ID included in the acquired puncture-related information (hereinafter, referred to as "biopsy needle information") from the biopsy needle information database 76B. In addition, the CPU 72 controls the display unit of the operation panel 29 to display the biopsy needle movement support screen having a predetermined configuration using the read-out biopsy needle information.

Figure 10:
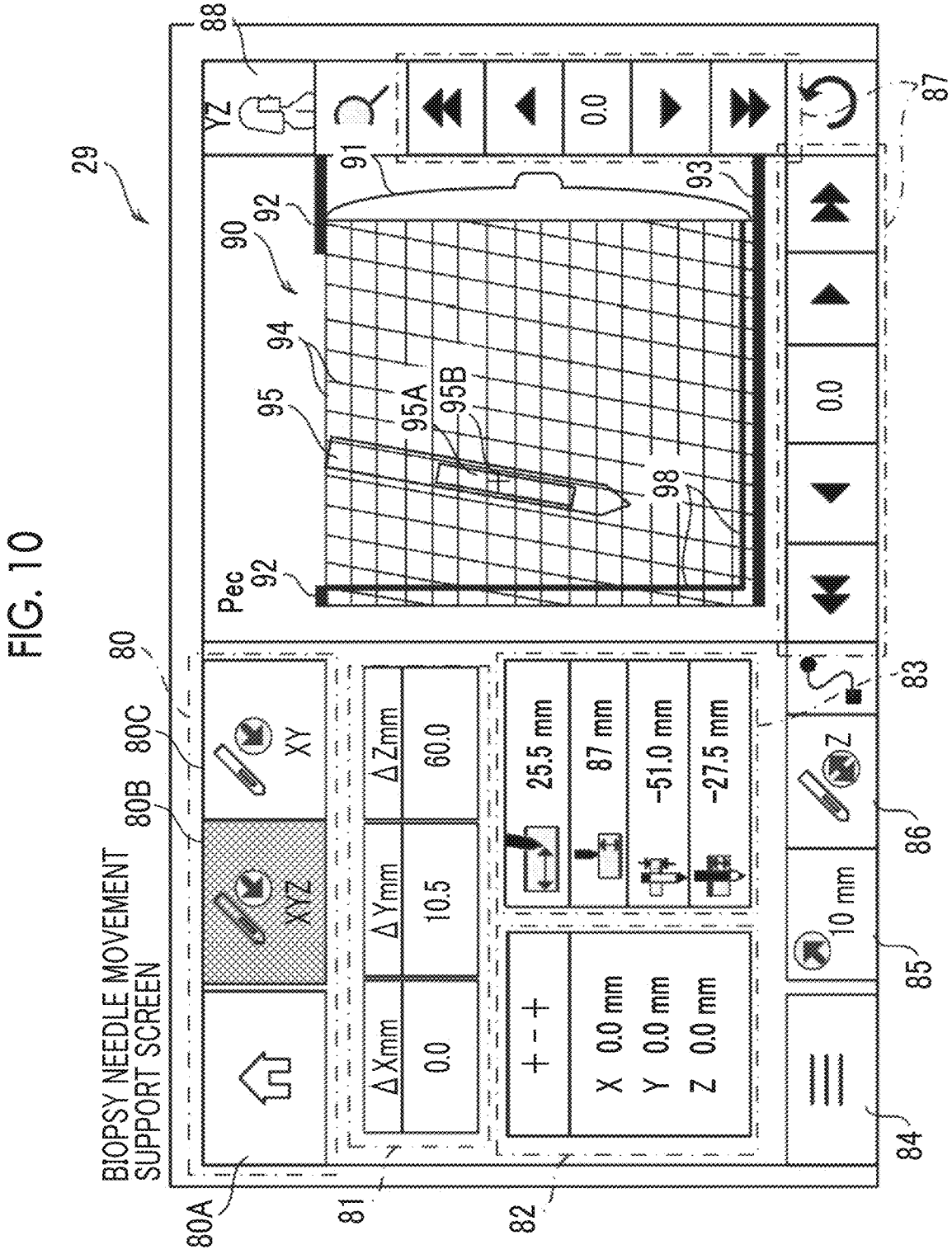
FIG. 10 is a front view illustrating an example of a biopsy needle movement support screen according to the embodiment.

As illustrated in FIG. 10, the biopsy needle movement support screen according to the present embodiment includes a target determination button display region 80, which is a region for displaying a button that is for determining a target position of the biopsy needle 21 and is designated in a case where the movement of the biopsy needle 21 is started. Further, the biopsy needle movement support screen according to the present embodiment includes a deviation amount display region 81, which is a region for displaying a deviation amount between the actual position and the target position of the biopsy needle 21. Further, the biopsy needle movement support screen according to the present embodiment includes a difference display region 82, which is a region for displaying a difference between a default target position of the biopsy needle 21 indicated by the target position information included in the puncture-related information and an adjusted target position of the biopsy needle 21. Further, the biopsy needle movement support screen according to the present embodiment includes a distance display region 83, which is a region for displaying a distance between the actual position of the biopsy needle 21 and various reference positions. The target determination button display region 80 corresponds to an "operation reception region" in the technology of the present disclosure.

In the target determination button display region 80 according to the present embodiment, a home position designation button 80A, which is designated in a case where the target position of the biopsy needle 21 is determined at a predetermined home position and movement of the biopsy needle 21 is started to the target position, is displayed. In addition, in the target determination button display region 80 according to the present embodiment, an XYZ direction movement designation button 80B, which is designated in a case where the actual target position of the biopsy needle 21 is determined as the target position of the biopsy needle 21 that is set at that time and movement of the biopsy needle 21 to the target position is started in three-dimensional directions including the X direction, the Y direction, and the Z direction, is displayed. Further, in the target determination button display region 80 according to the present embodiment, an XY direction movement designation button 80C, which is designated in a case where the actual target position of the biopsy needle 21 is determined as the target position of the biopsy needle 21 that is set at that time and movement of the biopsy needle 21 is started in two-dimensional directions including the X direction and the Y direction without movement in the Z direction, is displayed.

Note that, in the biopsy unit 26 according to the present embodiment, in order to actually start the movement of the biopsy needle 21, any one of the buttons displayed in the target determination button display region 80 is designated, and then a puncture execution button (not illustrated) which is provided as a hard switch on the operation panel 29 is pressed. On the other hand, the present disclosure is not limited thereto. For example, a form in which the movement of the biopsy needle 21 is immediately started by designating any button of the buttons displayed in the target determination button display region 80 may be adopted.

In addition, in the deviation amount display region 81 according to the present embodiment, regions for individually displaying deviation amounts between the actual position and the target position of the biopsy needle 21 in each of the X direction, the Y direction, and the Z direction are provided. Regions immediately below the display regions of "ΔXmm", "ΔYmm", and "ΔZmm" in FIG. 10 correspond to these individual display regions. Similarly, in the difference display region 82 according to the present embodiment, regions for individually displaying differences between the default target position of the biopsy needle 21 (the position indicated by the target position information that is input via the console 60) and the adjusted target position of the biopsy needle 21 in each of directions including the X direction, the Y direction, and the Z direction are provided.

In addition, in the distance display region 83 according to the present embodiment, a display region (in the example illustrated in FIG. 10, a region in which "25.5 mm" is displayed) for a distance between a chest wall of the subject and a needle tip of the actual biopsy needle 21, and a display region (in the example illustrated in FIG. 10, a region in which "87 mm" is displayed) for a distance between the imaging surface of the imaging table 14 and a needle tip of the actual biopsy needle 21 are provided.

In addition, in the distance display region 83 according to the present embodiment, a display region (in the example illustrated in FIG. 10, a region in which "−51.0 mm" is displayed) for a distance between a target tissue of the puncture and an end portion of the actual biopsy needle 21 on a side near to the opening portion 21A, and a display region (in the example illustrated in FIG. 10, a region displayed as "−27.5 mm") for a distance between the compression plate 18 and an upper end portion of the opening portion 21A of the actual biopsy needle 21 are provided.

Note that, by referring to the distance between the target tissue of the puncture and the end portion of the actual biopsy needle 21 on a side near to the opening portion 21A, it is possible to confirm whether or not the target tissue can be collected through the opening portion 21A of the biopsy needle 21. In addition, by referring to the distance between the compression plate 18 and the upper end portion of the opening portion 21A of the actual biopsy needle 21, it is possible to confirm whether or not the entire opening portion 21A of the biopsy needle 21 is positioned inside the breast M. In a state where a part of the opening portion 21A of the biopsy needle 21 is positioned outside the breast M, in a case where suction of the tissue is performed, the breast M is damaged. Thus, by confirming whether or not the entire opening portion 21A of the biopsy needle 21 is positioned inside the breast M, it is possible to prevent a damage to the breast M.

Further, on the biopsy needle movement support screen according to the present embodiment, a menu display button 84 that is designated in a case where various menus are displayed, a shortcut button 85 that is designated in a case where a shortcut for moving the biopsy needle 21 by a predetermined distance at once is performed, and a shortcut confirmation button 86 that is designated for confirming the execution of the shortcut are displayed.

Further, the biopsy needle movement support screen according to the present embodiment includes an adjustment button display region 87 that is a region in which a button designated to adjust the target position of the biopsy needle 21 is displayed, a direction display region 88 that is a region in which an icon indicating a direction of the body of the subject is displayed, and a schema diagram display region 90 that is a region in which a schema diagram is displayed. Note that, in the example illustrated in FIG. 10, a case where the body of the subject faces the X direction is illustrated in the direction display region 88. The image displayed in the direction display region 88 corresponds to a "third image" in the technology of the present disclosure.

In the schema diagram display region 90 according to the present embodiment, a target image 91 indicating the target object (in the present embodiment, the breast M) from which the tissue is to be collected by the biopsy needle 21 in a direction corresponding to the direction of the body of the subject displayed in the direction display region 88 is displayed. In addition, in the schema diagram display region 90 according to the present embodiment, an additional image 92 indicating the compression plate 18 and an additional image 93 indicating the imaging table 14 are displayed. Further, in the schema diagram display region 90 according to the present embodiment, a first image 95 indicating the target position of the biopsy needle 21 is displayed.

In the present embodiment, as the first image 95, an image, which is obtained by imitating the actually-used biopsy needle 21 and is indicated by the image information included in the read-out biopsy needle information, is applied. In addition, in the schema diagram display region 90 according to the present embodiment, the first image 95 is displayed such that a center position of an opening portion image 95A indicating the opening portion 21A is a target position indicated by the target position information included in the acquired puncture-related information. Further, in the present embodiment, a first mark 95B is displayed at the center position of the opening portion image 95A, that is, the position of the target tissue of the puncture. In the present embodiment, as the first mark 95B, a mark indicating addition (+) is applied. On the other hand, the present disclosure is not limited thereto. For example, a mark having any shape can be applied as the first mark 95B as long as the mark can be distinguished from other display contents, such as a mark indicating multiplication (×).

In addition, in the schema diagram display region 90 according to the present embodiment, auxiliary lines 94 disposed at equal intervals in the region including the first image 95 and the target image 91 are displayed. Here, in the schema diagram display region 90 according to the present embodiment, the auxiliary lines 94 are inclined and displayed in accordance with the traveling direction of the biopsy needle 21 toward the target object. Further, in the schema diagram display region 90 according to the present embodiment, a boundary line 98 with a region where a problem may occur in a case where the biopsy needle 21 is moved is displayed. On the other hand, in a case where a region in which a problem may occur is not a region into which the biopsy needle 21 can be inserted, the CPU 72 performs control for prohibiting the control to display the boundary line 98.

On the other hand, in the adjustment button display region 87 according to the present embodiment, a button group (hereinafter, referred to as a "target position adjustment button group") for adjusting the position of the first image 95 displayed in the schema diagram display region 90, that is, the target position of the puncture is displayed. As illustrated in FIG. 10, the target position adjustment button group according to the present embodiment includes two types of button groups, that is, a button group for moving the first image 95 in a right-left direction in FIG. 10 and a button group for moving the first image 95 in an up-down direction in FIG. 10. By operating these button groups, the position of the first image 95, furthermore, the target position of the puncture can be adjusted.

Therefore, in step 104, the CPU 72 determines whether or not any button of the target position adjustment button group displayed in the adjustment button display region 87 is operated by an operator (hereinafter, referred to as an "operator") of the mammography apparatus 2. In addition, in a case where a determination result in the determination is No, the processing proceeds to step 108. On the other hand, in a case where a determination result in the determination is Yes, it is assumed that an instruction to adjust the target position is received, and the processing proceeds to step 106.

In step 106, the CPU 72 moves the first image 95 in a direction according to the operation by the operator by a distance according to the operated button. In step 108, the CPU 72 determines whether or not the above-described puncture execution button is pressed after any button displayed in the target determination button display region 80 is designated by the operator. In a case where a determination result is No, the CPU 72 returns to step 104. In a case where a determination result is Yes, the CPU 72 assumes that adjustment of the target position is ended, and transitions to step 110.

Figure 11:
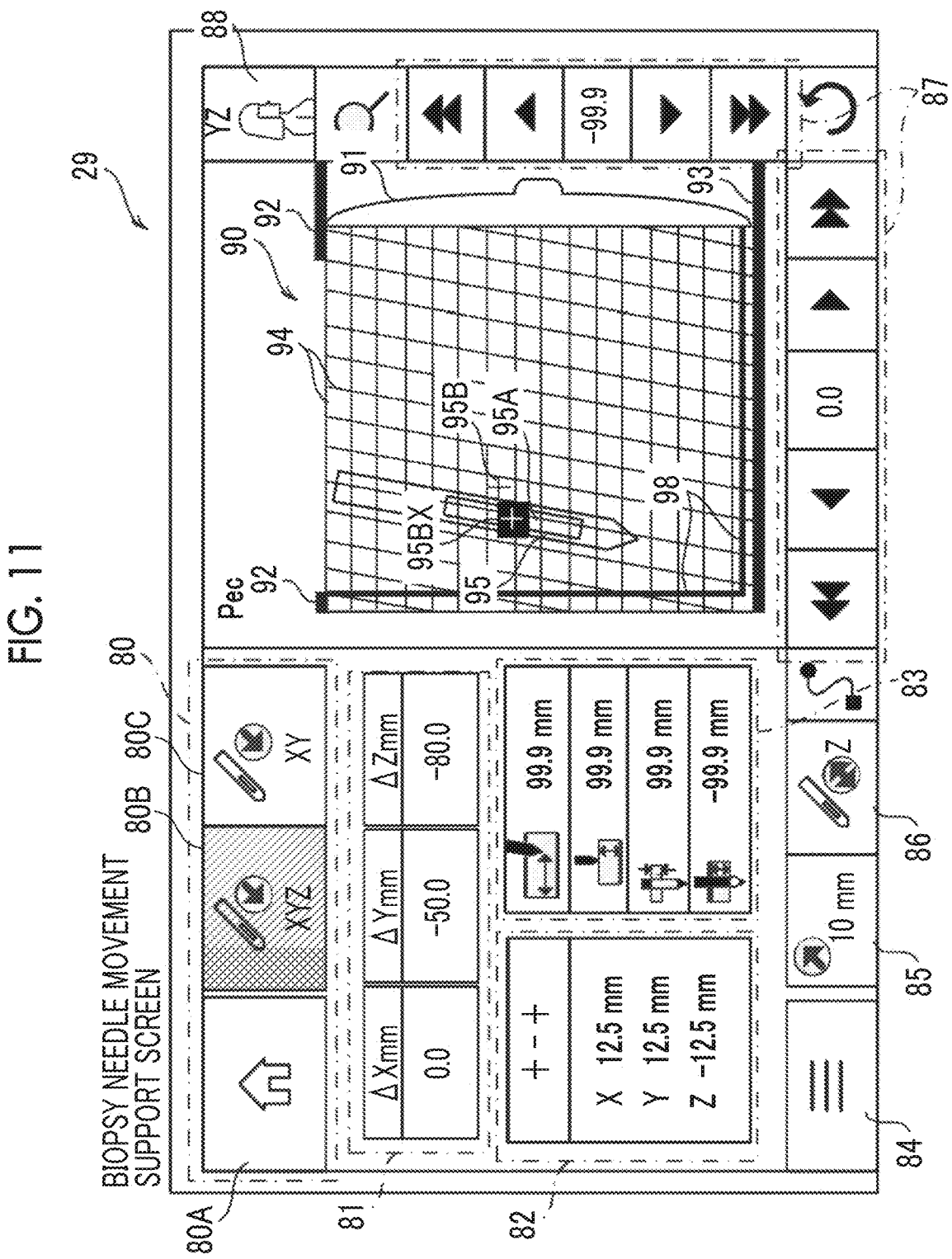
FIG. 11 is a front view illustrating another example of the biopsy needle movement support screen according to the embodiment.

Note that, in the biopsy needle movement processing according to the present embodiment, in a case where the repeating processing of step 104 to step 108 is executed, as illustrated in FIG. 11 as an example, the CPU 72 keeps the display position of the first mark 95B at the position in the initial state (default state), and displays a second mark 95BX corresponding to the first mark 95B in the first image 95 moved by the operation of the operator in a state different from the first mark 95B. In the example illustrated in FIG. 11, a case where the second mark 95BX is used as a reverse display (black and white inversion display) of the first mark 95B is illustrated. On the other hand, the present disclosure is not limited to the form. For example, a form in which any one of the first mark 95B or the second mark 95BX is displayed in a blinking manner may be adopted. For example, a form in which the first mark 95B and the second mark 95BX are different in at least one of a shape, a color, a size, or a shading may be adopted.

In step 110, the CPU 72 assumes that the position indicated by the second mark 95BX in the first image 95 at that time is the adjusted target position, and updates the target position information to information indicating the adjusted target position.

In step 112, the CPU 72 starts movement of the biopsy needle 21 to the target position indicated by the target position information. In step 114, the CPU 72 updates the biopsy needle movement support screen to update various types of information which change in accordance with the movement of the biopsy needle 21. In step 116, the CPU 72 determines whether or not the position of the biopsy needle 21 matches the target position indicated by the target position information. In a case where a determination result is No, the CPU 72 returns to step 114, and in a case where a determination result is Yes, the CPU 72 transitions to step 118.

Figure 12:
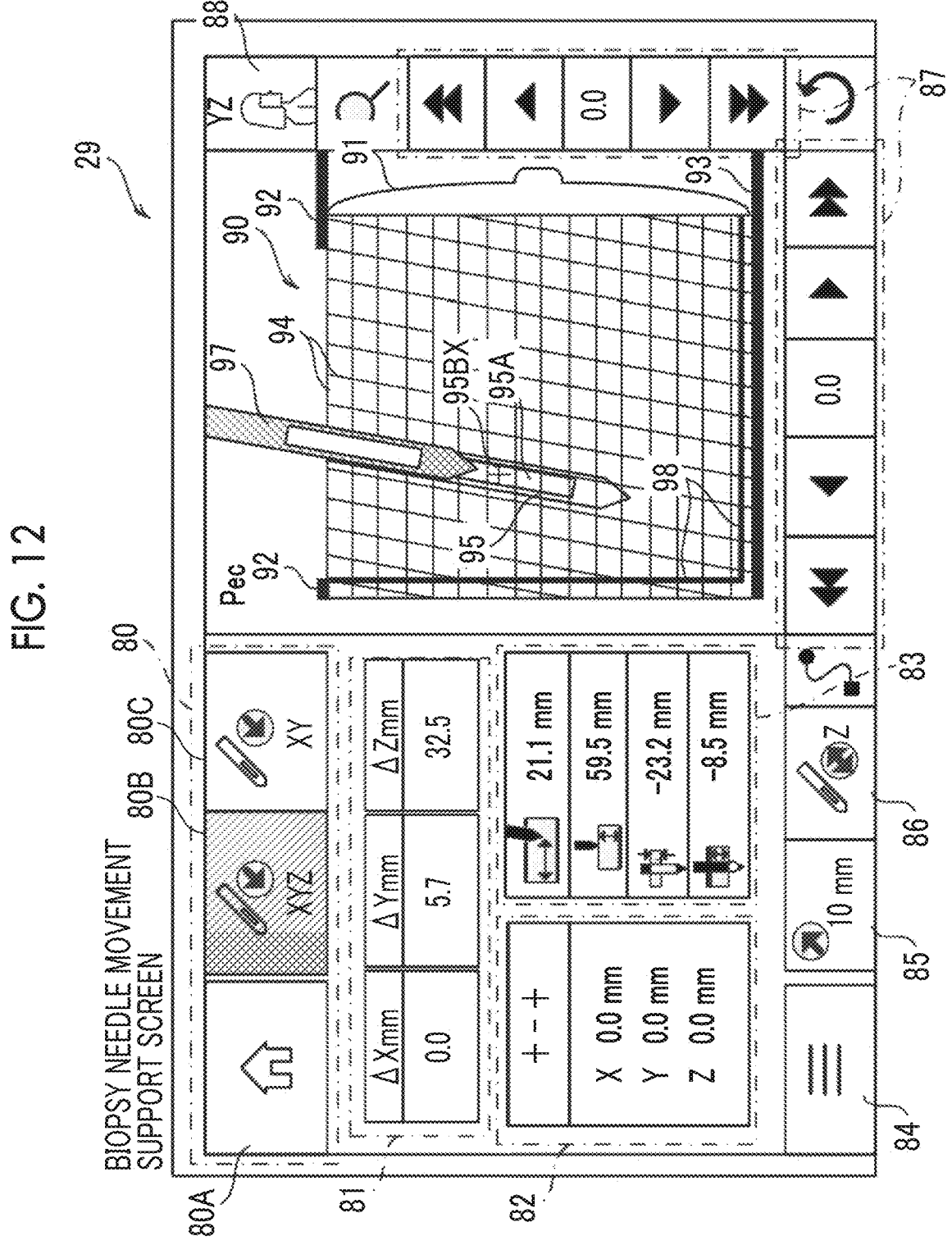
FIG. 12 is a front view illustrating still another example of the biopsy needle movement support screen according to the embodiment.

In a case where the processing of step 114 to step 116 is repeatedly executed, the actual biopsy needle 21 gradually approaches the target position indicated by the first image 95. For this reason, values displayed in each of the deviation amount display region 81 and the distance display region 83 on the biopsy needle movement support screen are sequentially changed. In addition, in a case where the biopsy needle 21 enters a region corresponding to the schema diagram display region 90, as illustrated in FIG. 12 as an example, the CPU 72 displays the second image 97 indicating the actual biopsy needle 21 in a state different from the first image 95 in the schema diagram display region 90.

Figure 13:
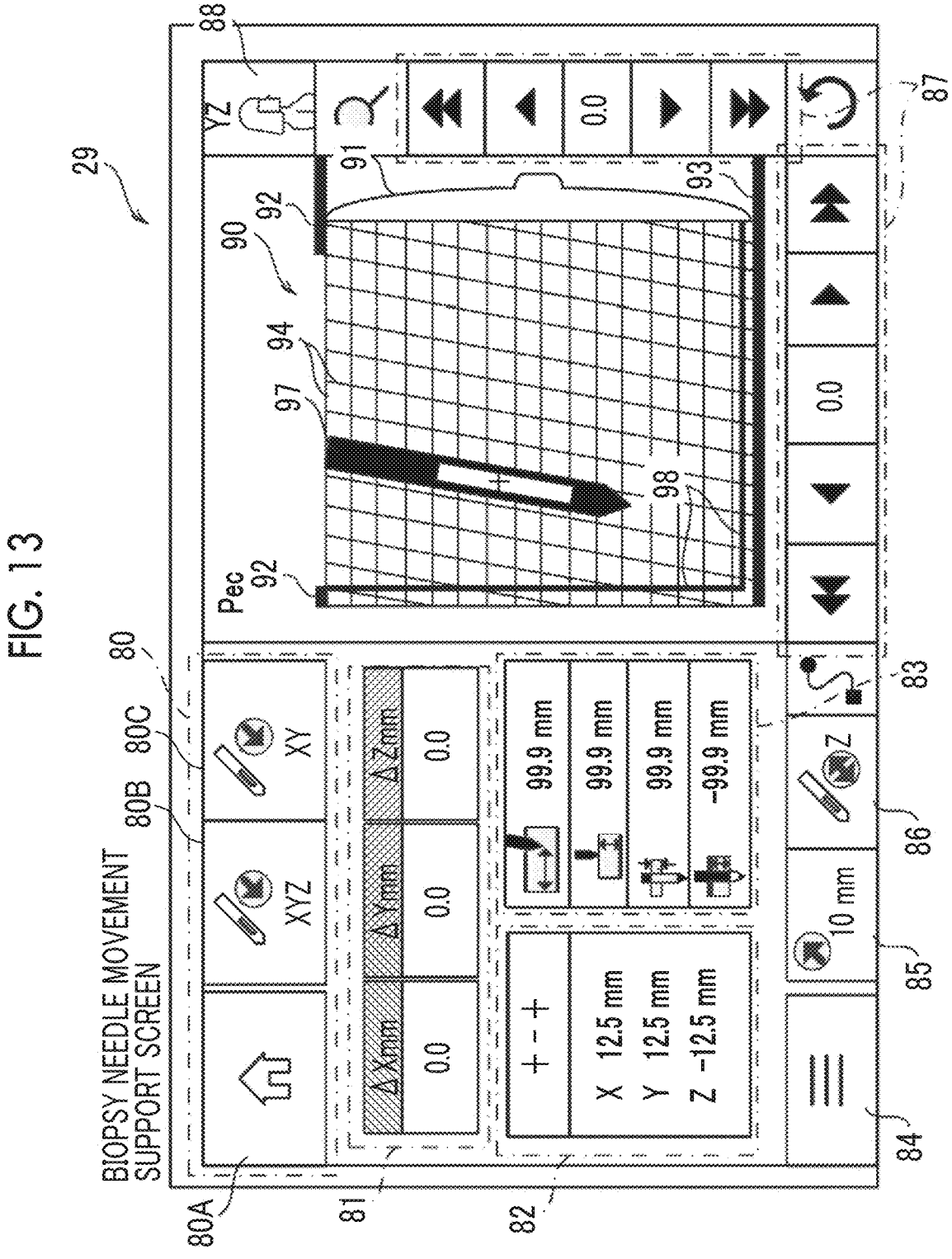
FIG. 13 is a front view illustrating still another example of the biopsy needle movement support screen according to the embodiment.

In addition, in a case where the position of the biopsy needle 21 matches the target position, as illustrated in FIG. 13 as an example, the CPU 72 changes a display state of the second image 97 to a state different from the previous state. Note that, in the example illustrated in FIG. 13, a case where the second image 97 is changed to a solid black image has been exemplified. On the other hand, the present disclosure is not limited thereto. For example, a form in which a color, a shading, a pattern, or the like of the filling of the second image 97 is displayed in a state different from the previous state may be adopted, or a form in which a color, a thickness, a display form, or the like of an outer peripheral line of the second image 97 is displayed in a state different from the previous state may be adopted.

In addition, in a case where the position of the biopsy needle 21 matches the target position, as illustrated in FIG. 13 as an example, the CPU 72 sets the display state of the above-described operation reception region (in the present embodiment, the target determination button display region 80) to a state different from the previous display state. Note that, in the example illustrated in FIG. 13, a case where a hatched state of the button, which is in a hatched state by being designated by the operator in the target determination button display region 80, is changed to a non-hatched state is illustrated. On the other hand, it is needless to say that the present disclosure is not limited thereto.

Further, in a case where the position of the biopsy needle 21 matches the target position, the CPU 72 performs control such that the biopsy needle 21 is not moved to the insertion side of the target object. As described above, by this control, it is possible to prevent the biopsy needle 21 from being inserted to an unnecessary depth.

In step 118, the CPU 72 stops the movement of the biopsy needle 21, and performs suction of the tissue to collect the tissue by controlling the biopsy needle 21. In step 120, the CPU 72 starts retraction of the biopsy needle 21 from the target position.

In step 122, the CPU 72 updates the biopsy needle movement support screen to update various types of information which change in accordance with the movement of the biopsy needle 21. In step 124, the CPU 72 determines whether or not the position of the biopsy needle 21 is a standby position which is set in advance. In a case where a determination result is No, the CPU 72 returns to step 122. On the other hand, in a case where a determination result is Yes, the CPU 72 ends the biopsy needle movement processing.

In a case where the processing of step 122 to step 124 is repeatedly executed, the actual biopsy needle 21 gradually deviates from the target position indicated by the first image 95. For this reason, values displayed in each of the deviation amount display region 81 and the distance display region 83 on the biopsy needle movement support screen are sequentially changed in a direction opposite to the direction in the case where the biopsy needle 21 approaches the target position.

Figure 14:
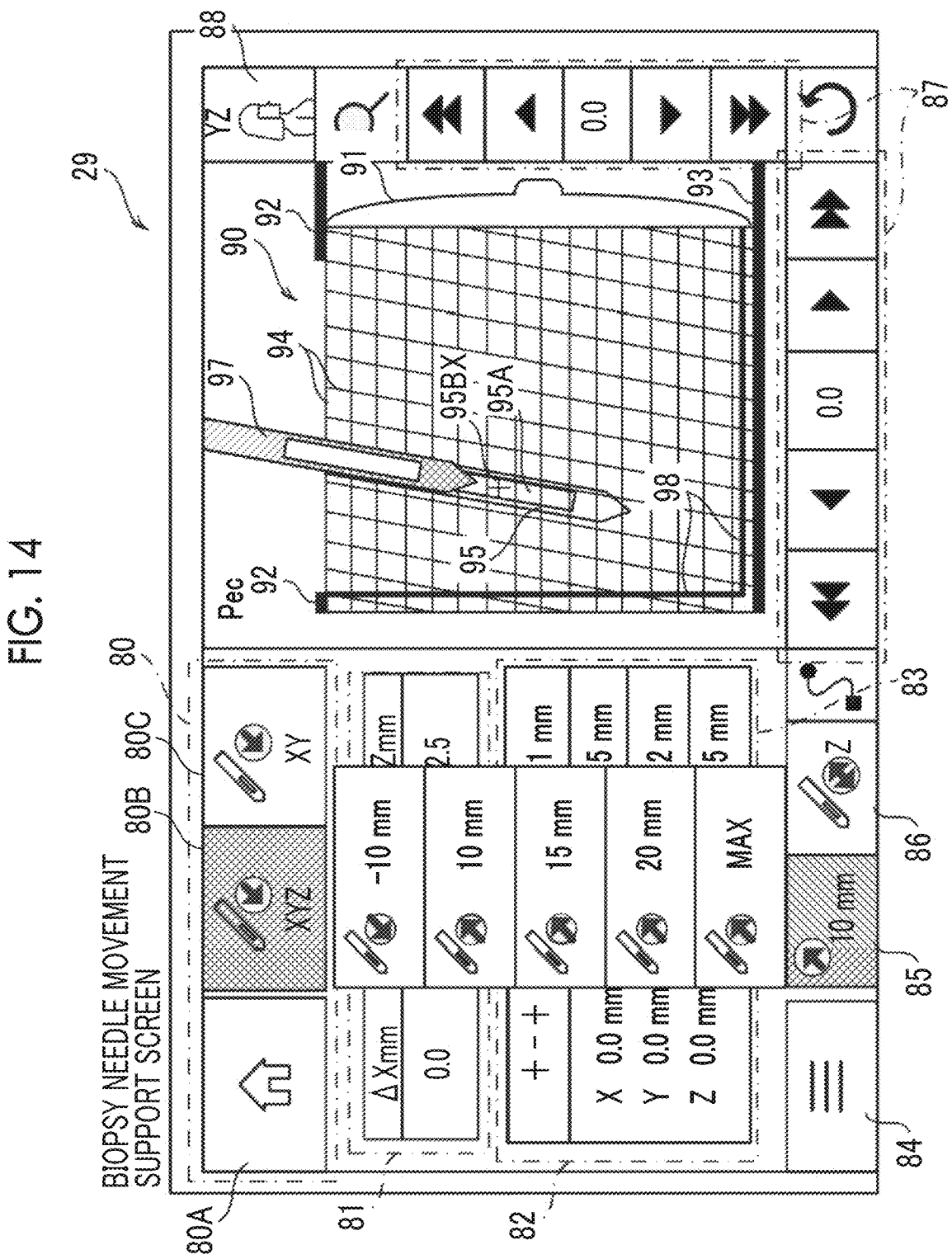
FIG. 14 is a front view illustrating still another example of the biopsy needle movement support screen according to the embodiment.

Note that, as described above, in a case where the biopsy needle 21 is to be moved at once, the operator designates the shortcut button 85. In response to this designation, as illustrated in FIG. 14 as an example, a plurality of buttons are displayed on the biopsy needle movement support screen, the plurality of buttons in which combinations of a plurality of types of movement distances and movement directions (in the example illustrated in FIG. 14, two directions of an approach direction and a retraction direction) for the biopsy needle 21 are individually displayed. Therefore, in a case where the operator designates the button in which a desired combination is displayed, the movement of the biopsy needle 21 corresponding to the combination can be performed.

Note that, in the biopsy unit 26 according to the present embodiment, instead of immediately moving the biopsy needle 21 in a case where any one of the plurality of buttons displayed by designating the shortcut button 85 is designated, in a case where the button is designated and then the shortcut confirmation button 86 is designated, the actual movement is performed. Here, the present disclosure is not limited thereto. A form in which the biopsy needle 21 is immediately moved in a case where any one of the plurality of buttons is designated without waiting for designation of the shortcut confirmation button 86 may be adopted.

As described above, according to the biopsy device (in the present embodiment, the biopsy unit 26) according to the present embodiment, control is performed such that the target image indicating the target object from which the tissue is to be collected by the biopsy needle 21, the first image indicating the target position of the biopsy needle 21, and the second image indicating the actual position of the biopsy needle 21 are displayed in the same display diagram with a common two-dimensional coordinate system and the first image and the second image are displayed in different states. Therefore, as compared with the technology in the related art, it is possible to easily compare the target state of the biopsy needle 21 with the actual state of the biopsy needle 21.

Further, with the biopsy device according to the present embodiment, in a case where the first image and the second image overlap with each other by the movement operation of the biopsy needle 21, control to display at least one of the first image or the second image in a state different from the previous display state is performed. Therefore, it is possible to more easily recognize that the biopsy needle 21 reaches the target state.

Further, with the biopsy device according to the present embodiment, in a case where the first image and the second image overlap with each other by the movement operation of the biopsy needle 21, the display state of the operation reception region (in the present embodiment, the target determination button display region 80) is set to a state different from the previous display state. Therefore, it is possible to more easily recognize that the biopsy needle 21 reaches the target state.

Further, with the biopsy device according to the present embodiment, in a case where the first image and the second image overlap with each other by the movement operation of the biopsy needle 21, control is performed such that the biopsy needle 21 is not moved to the insertion side of the target object. Therefore, it is possible to prevent the biopsy needle 21 from being inserted to an unnecessary depth.

Further, with the biopsy device according to the present embodiment, control to display the auxiliary lines 94 disposed at equal intervals in the region including the first image and the target image is further performed. Therefore, it is possible to more accurately recognize the deviation amount between the actual state and the target state of the biopsy needle 21.

Further, with the biopsy device according to the present embodiment, control is performed such that the auxiliary lines 94 are inclined and displayed in accordance with the traveling direction of the biopsy needle 21 toward the target object. Therefore, it is possible to more accurately recognize the deviation amount between the actual state and the target state of the biopsy needle 21.

Further, with the biopsy device according to the present embodiment, control to display the third image indicating the direction of the body of the subject including the target object is further performed. Therefore, it is possible to more easily recognize the puncture state of the biopsy needle 21 with respect to the subject.

Further, with the biopsy device according to the present embodiment, in a case where an instruction to adjust the position of the first image is received, control to display the first mark indicating the position in the initial state and the second mark indicating the adjusted position in different states is further performed. Therefore, it is possible to more easily recognize that the target state of the biopsy needle 21 is adjusted.

Further, with the biopsy device according to the present embodiment, control to display the boundary line 98 with the region in which a problem may occur in a case where the biopsy needle 21 is moved is further performed. Therefore, it is possible to prevent occurrence of a problem due to the movement of the biopsy needle 21 in advance.

Further, with the biopsy device according to the present embodiment, in a case where the region where a problem may occur is not the region into which the biopsy needle 21 can be inserted, control to display the boundary line 98 is prohibited. Therefore, it is possible to avoid unnecessary displaying of the boundary line 98.

Further, with the biopsy device according to the present embodiment, control to display the additional image 92 and the additional image 93 indicating the imaging table 14 and the compression plate 18 is further performed. Therefore, it is possible to recognize a relative position relationship between the positions of the imaging table 14 and the compression plate 18 and the biopsy needle 21.

Further, with the biopsy device according to the present embodiment, both the first image and the second image are images in which the biopsy needle 21 is symbolized. Therefore, the first image and the second image can be more easily displayed as compared with a case where these images are images of the actual biopsy needle 21.

Note that, in the embodiment, a case where the CPU 72 provided in the controller 70 of the biopsy unit 26 is applied as the processor according to the technology of the present disclosure has been described. On the other hand, the present disclosure is not limited thereto. For example, a form in which the CPU provided in the controller 50 of the mammography apparatus 2 is applied as a processor according to the technology of the present disclosure may be adopted.

Further, in the embodiment, the biopsy needle movement support screen in a case where the subject faces the X direction is illustrated in FIG. 10 to FIG. 14. On the other hand, the present disclosure is not limited thereto.

Figure 15:
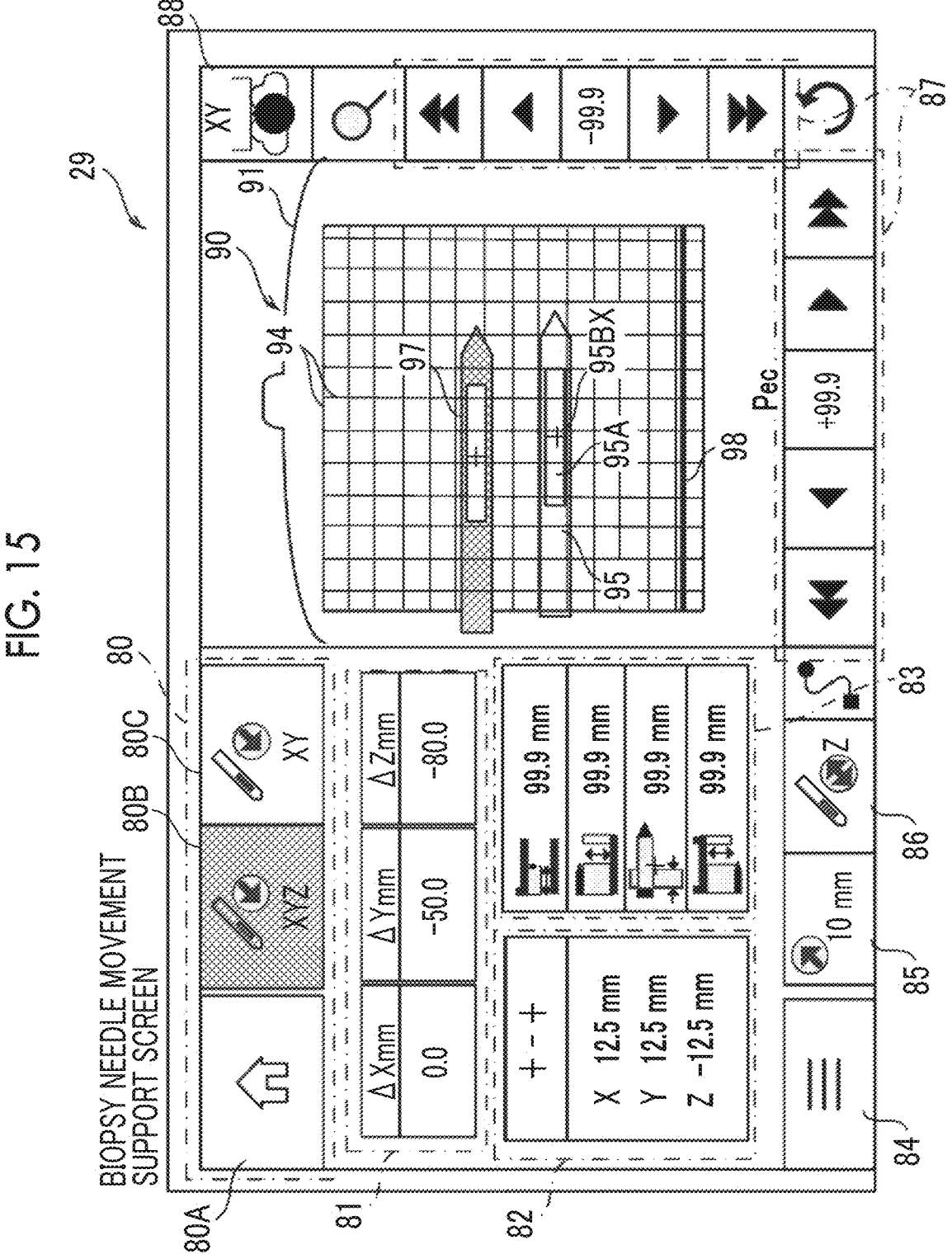
FIG. 15 is a front view illustrating still another example of the biopsy needle movement support screen according to the embodiment.
Figure 16:
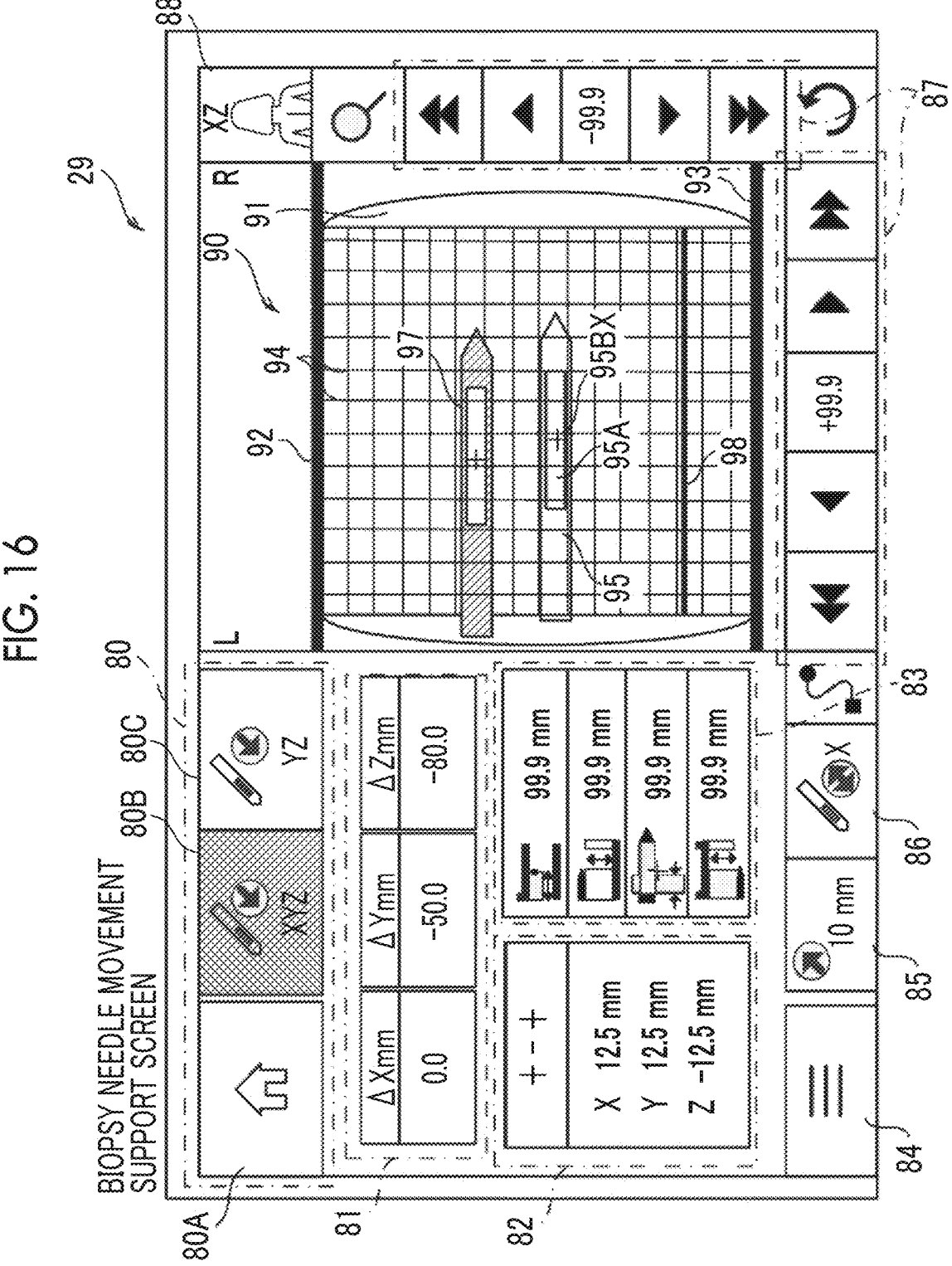
FIG. 16 is a front view illustrating still another example of the biopsy needle movement support screen according to the embodiment.
Figure 17:
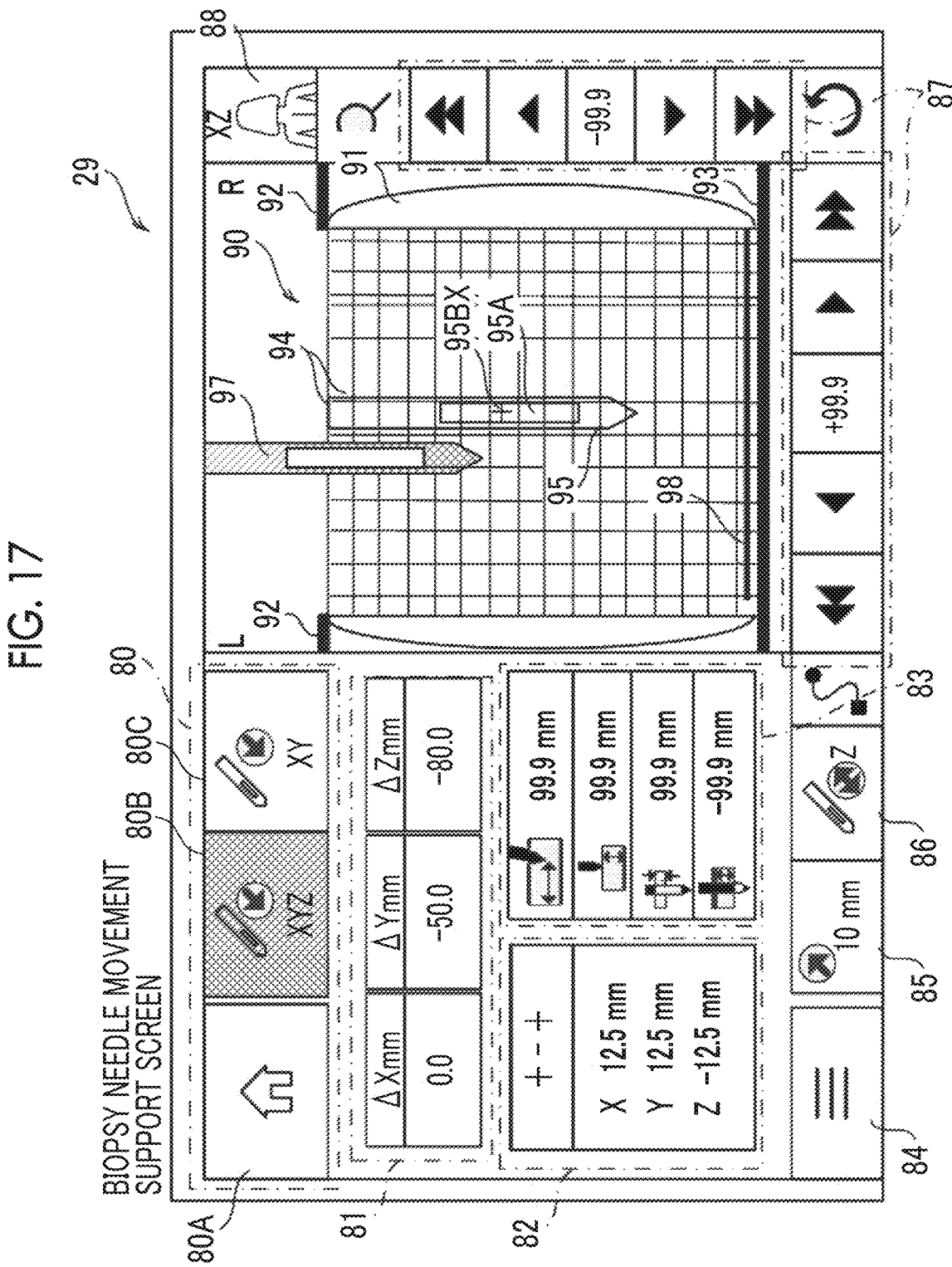
FIG. 17 is a front view illustrating still another example of the biopsy needle movement support screen according to the embodiment.

FIG. 15 illustrates an example of the biopsy needle movement support screen in a case where the subject faces the Z direction, and FIG. 16 and FIG. 17 illustrate an example of the biopsy needle movement support screen in a case where the subject faces the Y direction. Note that FIG. 16 illustrates a case where a biopsy needle 21 for lateral puncture is applied as the biopsy needle 21 and FIG. 17 illustrates a case where a biopsy needle 21 for longitudinal puncture is applied as the biopsy needle 21.

Even in these forms, the same effects as those described in the embodiment can be obtained.

Note that, in the embodiment, for example, as a hardware structure of processing units that execute various types of processing, such as the display controller 72A and the movement controller 72B, the following various processors can be used. As described above, the various processors include, in addition to the CPU that is a general-purpose processor that executes software (program) to function as various processing units, a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. In this manner, the various processing units are configured by using one or more various processors as a hardware structure.

Furthermore, as the hardware structure of the various processors, more specifically, an electrical circuit (circuitry) in which circuit elements such as semiconductor elements are combined can be used.

Further, in the embodiment, the aspect in which the biopsy needle movement processing program 76A is stored (installed) in advance in the storage unit 76 of the biopsy unit 26 has been described. On the other hand, the present disclosure is not limited thereto. The biopsy needle movement processing program 76A may be provided by being recorded in a recording medium, such as a compact disc read only memory (CD-ROM), a digital versatile disc read only memory (DVD-ROM), or a universal serial bus (USB) memory. Further, the biopsy needle movement processing program 76A may be downloaded from an external device through a network.

From the above description, the inventions described in following Appendices can be understood.

Appendix 1

A biopsy device comprising:
at least one processor,
in which the processor is configured to:
    perform control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states.

Appendix 2

The biopsy device according to Appendix 1,
in which the processor is configured to:
in a case where the first image and the second image overlap with each other by a movement operation of the biopsy needle, perform control such that at least one of the first image or the second image is displayed in a state different from a previous display state.

Appendix 3

The biopsy device according to Appendix 2,
in which the processor is configured to:
further perform control to display, separately from the display diagram, an operation reception region for receiving an input of an operation instruction for the biopsy needle; and
in a case where the first image and the second image overlap with each other by a movement operation of the biopsy needle, set a display state of the operation reception region to a state different from a previous display state.

Appendix 4

The biopsy device according to Appendix 2 or 3,
in which the processor is configured to:
in a case where the first image and the second image overlap with each other by a movement operation of the biopsy needle, perform control such that the biopsy needle is not moved to an insertion side of the target object.

Appendix 5

The biopsy device according to any one of Appendixes 1 to 4,
in which the processor is configured to:
further perform control to display auxiliary lines disposed at equal intervals in a region including the first image and the target image in the display diagram.

Appendix 6

The biopsy device according to Appendix 5,
in which the processor is configured to:
perform control to incline and display the auxiliary lines in accordance with a traveling direction of the biopsy needle toward the target object.

Appendix 7

The biopsy device according to any one of Appendixes 1 to 6,
in which the processor is configured to:
further perform control to display a third image indicating a direction of a body of a subject including the target object, separately from the display of the display diagram.

Appendix 8

The biopsy device according to any one of Appendixes 1 to 7,
in which the processor is configured to:
in a case where an instruction to adjust the position of the first image is received, further perform control to display a first mark indicating the position in an initial state and a second mark indicating the adjusted position in different states.

Appendix 9

The biopsy device according to any one of Appendixes 1 to 8,
in which the processor is configured to:
further perform control to display, in the display diagram, a boundary line with a region where a problem may occur in a case where the biopsy needle is moved.

Appendix 10

The biopsy device according to Appendix 9,
in which the processor is configured to:
in a case where the region where a problem may occur is not a region into which the biopsy needle is allowed to be inserted, prohibit control to display the boundary line.

Appendix 11

The biopsy device according to any one of Appendixes 1 to 10,
in which the processor is configured to:
in a case where the biopsy needle punctures a breast as the target object in a state where the breast is compressed by a compression plate against an imaging table of a mammography apparatus, further perform control to display an additional image indicating at least one of the imaging table or the compression plate.

Appendix 12

The biopsy device according to any one of Appendixes 1 to 11,
in which the first image is an image indicating the target position and a target direction of the biopsy needle, and the second image is an image indicating the actual position and an actual direction of the biopsy needle.

Appendix 13

The biopsy device according to any one of Appendixes 1 to 12,
in which at least one of the first image or the second image is an image in which the biopsy needle is symbolized.

Appendix 14

A program causing a computer to execute a process comprising:
performing control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states.

What is claimed is:

1. A biopsy device comprising:
at least one processor,
wherein the at least one processor is configured to:
  perform control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states,
  perform control to display auxiliary lines disposed at equal intervals in a region including the first image and the target image in the display diagram, and
  perform control to change an orientation of the auxiliary lines in accordance with a traveling direction of the biopsy needle toward the target object, and to display the auxiliary lines.

2. The biopsy device according to claim 1,
wherein the at least one processor is configured to:
in a case where the first image and the second image overlap with each other by a movement operation of the biopsy needle, perform control such that at least one of the first image or the second image is displayed in a state different from a previous display state.

3. The biopsy device according to claim 2,
wherein the at least one processor is configured to:
further perform control to display, separately from the display diagram, an operation reception region for receiving an input of an operation instruction for the biopsy needle; and
in the case where the first image and the second image overlap with each other by the movement operation of the biopsy needle, set a display state of the operation reception region to a state different from a previous display state.

4. The biopsy device according to claim 3,
wherein the at least one processor is configured to:
in the case where the first image and the second image overlap with each other by the movement operation of the biopsy needle, perform control such that the biopsy needle is not moved to an insertion side of the target object.

5. The biopsy device according to claim 2,
wherein the at least one processor is configured to:
in the case where the first image and the second image overlap with each other by the movement operation of the biopsy needle, perform control such that the biopsy needle is not moved to an insertion side of the target object.

6. The biopsy device according to claim 1,
wherein the at least one processor is configured to:
further perform control to display a third image indicating a direction of a body of a subject including the target object, separately from the display of the display diagram.

7. The biopsy device according to claim 1,
wherein the at least one processor is configured to:
in a case where an instruction to adjust the position of the first image is received, further perform control to display a first mark indicating the position in an initial state and a second mark indicating the adjusted position in different states.

8. The biopsy device according to claim 1,
wherein the at least one processor is configured to:
further perform control to display, in the display diagram, a boundary line with a region where a problem may occur in a case where the biopsy needle is moved.

9. The biopsy device according to claim 8,
wherein the at least one processor is configured to:
in a case where the region where the problem may occur is not a region into which the biopsy needle is allowed to be inserted, prohibit control to display the boundary line.

10. The biopsy device according to claim 1,
wherein the at least one processor is configured to:
in a case where the biopsy needle punctures a breast as the target object in a state where the breast is compressed by a compression plate against an imaging table of a mammography apparatus, further perform control to display an additional image indicating at least one of the imaging table or the compression plate.

11. The biopsy device according to claim 1,
wherein the first image is an image indicating the target position and a target direction of the biopsy needle, and
the second image is an image indicating the actual position and an actual direction of the biopsy needle.

12. The biopsy device according to claim 1,
wherein at least one of the first image or the second image is an image in which the biopsy needle is symbolized.

13. A non-transitory computer-readable storage medium storing a program that causes a computer to execute a process, the process comprising:
  performing control to display a target image indicating a target object from which a tissue is to be collected by a biopsy needle, a first image indicating a target position of the biopsy needle, and a second image indicating an actual position of the biopsy needle in the same display diagram with a common two-dimensional coordinate system and to display the first image and the second image in different states,
  performing control to display auxiliary lines disposed at equal intervals in a region including the first image and the target image in the display diagram, and
  performing control to change an orientation of the auxiliary lines in accordance with a traveling direction of the biopsy needle toward the target object, and to display the auxiliary lines.

* * * * *